(12) United States Patent
Krueger

(10) Patent No.: US 9,289,521 B2
(45) Date of Patent: Mar. 22, 2016

(54) CONTAINER STERILIZATION APPARATUS AND METHOD

(71) Applicant: KRONES AG, Neutraubling (DE)

(72) Inventor: Jochen Krueger, Hagelstadt (DE)

(73) Assignee: Krones, AG, Neutraubling (DE)

( * ) Notice: Subject to any disclaimer, the term of this patent is extended or adjusted under 35 U.S.C. 154(b) by 300 days.

(21) Appl. No.: 13/906,977

(22) Filed: May 31, 2013

(65) Prior Publication Data

US 2013/0323118 A1    Dec. 5, 2013

(30) Foreign Application Priority Data

Jun. 1, 2012   (DE) .................. 10 2012 104 753

(51) Int. Cl.
*A61L 2/00* (2006.01)
*A61L 2/08* (2006.01)
*A61L 2/24* (2006.01)

(52) U.S. Cl.
CPC . *A61L 2/08* (2013.01); *A61L 2/087* (2013.01); A61L 2202/14 (2013.01); A61L 2202/23 (2013.01)

(58) Field of Classification Search
CPC .............................. A61L 2/87; A61L 2202/14
USPC ........................................................ 422/3, 22
See application file for complete search history.

(56) References Cited

U.S. PATENT DOCUMENTS

| | | | |
|---|---|---|---|
| 5,881,534 A * | 3/1999 | Ahlqvist et al. | ................ 53/403 |
| 6,949,222 B1 | 9/2005 | Moller et al. | |
| 7,553,446 B1 * | 6/2009 | Treece et al. | ................... 422/22 |
| 8,415,633 B2 | 4/2013 | Keil et al. | |
| 2003/0039579 A1 * | 2/2003 | Lambert et al. | ................. 422/22 |
| 2011/0016829 A1 | 1/2011 | Drenguis et al. | |
| 2011/0233414 A1 | 9/2011 | Keil et al. | |

FOREIGN PATENT DOCUMENTS

| | | |
|---|---|---|
| DE | 60016446 | 4/2005 |
| DE | 102008007428 | 8/2009 |
| DE | 102009034646 | 9/2010 |
| DE | 102009018210 | 11/2010 |
| EP | 0609709 | 8/1994 |
| JP | 2007126171 | 5/2007 |

OTHER PUBLICATIONS

Chinese OA dated Feb. 10, 2015 issued in corresponding Application No. 2013102165818.
Mittendorfer, J., et al., Radiation Physics and Chemistry, "Decontamination of Food Packaging Using Electron Beam-Status and Prospects," vol. 63, 2002, pp. 833-836.
Sugranes, Jorge A., Journal of Validation Technology, "Basic Operating Principles and Validation of Electron Beam Irradiation Systems," vol. 12, No. 1, 2005.
Search Report dated Jan. 23, 2013, issued in corresponding German Application No. 10 2012 104 753.7.

* cited by examiner

*Primary Examiner* — Kevin Joyner
(74) *Attorney, Agent, or Firm* — Onello & Mello, LLP

(57) ABSTRACT

Provided is an apparatus for sterilizing containers with a conveying device, which conveys the containers along a preset conveying path. A first sterilization device acts upon at least one area of the containers with radiation in order to sterilize them. A checking device is arranged downstream with respect to the first sterilization device along the conveying path in order to check the sterilization procedure. The checking device is used for analyzing at least one medium occurring in the region of the containers.

13 Claims, 1 Drawing Sheet

CONTAINER STERILIZATION APPARATUS AND METHOD

CROSS-REFERENCE TO RELATED APPLICATIONS

This application claims priority from German Patent Application No. 10 2012 104 753.7 filed on Jun. 1, 2012, the content of which is incorporated herein by reference in its entirety.

BACKGROUND

1. Field of the Inventive Concept

The present inventive concept relates to an apparatus for the sterilization of containers.

2. Description of the Related Art

Container sterilization devices have been known for a long time and are readily available. A well-known approach to sterilizing containers, in particular plastics material containers, includes the use of peracetic acid or hydrogen peroxide ($H_2O_2$).

SUMMARY

In one aspect, provided is an apparatus that sterilizes a plurality of containers, comprising: a conveying device that conveys the containers along a predetermined conveying path; a first sterilization device that sterilizes at least a portion of the plurality of containers with radiation; and a checking device constructed and arranged downstream with respect to the first sterilization device along the conveying path for checking a sterilization procedure.

In an embodiment, the checking device analyzes at least one gaseous medium occurring in a region proximal to the plurality of containers or a liquid medium in an interior region of at least one of the plurality of containers.

In an embodiment, the checking device includes a take-up element for drawing at least part of the gaseous medium or the liquid medium.

In an embodiment, the checking device includes a drawing-in element for drawing in at least one pre-set portion of the gaseous or liquid medium.

In an embodiment, the checking device includes a mass spectrometer.

In an embodiment, the checking device is constructed and arranged in a stationary position relative to a movement of the conveying path.

In an embodiment, the checking device includes a control device that causes a gaseous medium to be drawn in at least in part and/or a gaseous medium to be discharged at least for a time.

In an embodiment, the checking device is at least temporarily present in an area proximal to apertures of the sterilized containers for testing an area around the apertures or a medium thereabout or therein.

In an embodiment, the apparatus has at least one blasting device for cleaning the containers.

In accordance with another aspect, provided is a method of sterilizing containers, comprising: conveying the containers along a predetermined conveying path; sterilizing at least a portion of the plurality of containers with radiation; and checking a sterilization procedure after irradiating at least a portion of the plurality of containers.

In an embodiment, the method further comprises analyzing at least one of at least a part of a gaseous medium present in an area of a container of the plurality of containers or least part of a liquid medium originating in the container.

In an embodiment, the method further comprises analyzing the least part of the gaseous medium or the liquid medium during a movement of the containers.

In an embodiment, the method further comprises drawing the gaseous medium in at least for a time.

In an embodiment, a gaseous medium is blown into the containers before and/or during a checking of the gaseous medium.

BRIEF DESCRIPTION OF THE DRAWINGS

The above and other aspects and features of the present inventive concept will become more apparent by describing in detail exemplary embodiments thereof with reference to the attached drawings, in which.

DETAILED DESCRIPTION

Figure 1:
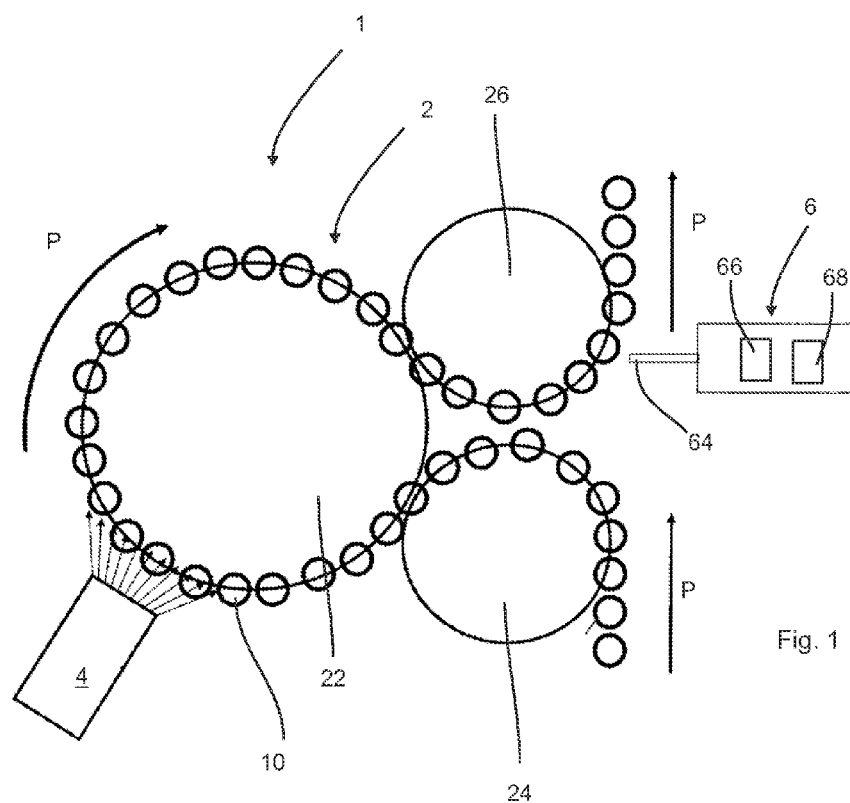
FIG. 1 is a diagram illustrating an apparatus according to embodiments of the present inventive concepts.

Exemplary embodiments in accordance with principles of inventive concepts will now be described more fully with reference to the accompanying drawings, in which exemplary embodiments are shown. Exemplary embodiments in accordance with principles of inventive concepts may, however, be embodied in many different forms and should not be construed as being limited to the embodiments set forth herein; rather, these embodiments are provided so that this disclosure will be thorough and complete, and will fully convey the concept of exemplary embodiments to those of ordinary skill in the art. Like reference numerals in the drawings denote like elements, and thus their description may not be repeated.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers indicate like elements throughout. As used herein the term "and/or" includes any and all combinations of one or more of the associated listed items. Other words used to describe the relationship between elements or layers should be interpreted in a like fashion (e.g., "between" versus "directly between," "adjacent" versus "directly adjacent," "on" versus "directly on"). It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of exemplary embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly. The terminology used herein is for the purpose of describing particular embodiments only and is not intended to be limiting of exemplary embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

Exemplary embodiments in accordance with principles of inventive concepts are described herein with reference to cross-sectional illustrations that are schematic illustrations of idealized embodiments (and intermediate structures) of exemplary embodiments. As such, variations from the shapes of the illustrations as a result, for example, of manufacturing techniques and/or tolerances, are to be expected. Thus, exemplary embodiments in accordance with principles of inventive concepts should not be construed as limited to the particular shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of exemplary embodiments.

Unless otherwise defined, all terms (including technical and scientific terms) used herein have the same meaning as commonly understood by one of ordinary skill in the art to which exemplary embodiments in accordance with principles of inventive concepts belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Recently, attempts have been made to dispense with the use of chemicals during the sterilization. Numerous apparatus are therefore also well-known for performing sterilization by means of radiation, for example electron radiation.

These methods allow a satisfactory sterilization of the containers, for example, the inner walls of the containers. However, it is relatively difficult to monitor the electron irradiation of the containers or the result of sterilization.

For monitoring the process of the electron beam sterilization, reliable evidence is required that each individual container, for example, a cup, a bottle, a plastics material bottle or pre-form, has received an adequate dose of electron energy or radiation energy respectively. In this way, it is necessary for example for a dose of 25 kGy to be applied without gaps to the entire surface of the container.

Various approaches are known for monitoring the reliable irradiation. In this way, it is known for example to measure and to monitor the electron flow. In this case for example, the electron flow of an emitter can be measured by means of a metallic plate and it can be brought into correlation with the sterilization effect during this flow. With this method, however, it is not possible for a measurement to be determined during the actual sterilization. In addition, it is also known for use to be made of a measurement and protection grid of an electron beam emitter. In this case part of the radiation is intercepted during the sterilization by means of a metallic grid instead of a metallic sheet and is evaluated quantitatively.

In addition, it is known for use to be made of a wire which permanently measures the intensity of the electron beam, for example, described in U.S. Pat. No. 6,560,714 B2, incorporated by reference herein in its entirety. These procedures have a drawback, however, that part of the beam or the radiation energy respectively is not available for the sterilization.

Other methods are known in which the parameters of the emitters are permanently monitored. In this way, it is proposed to monitor the radiation current and the radiation voltage, for example, described in German Application DE 2009 034 646 A1, incorporated by reference herein in its entirety. In addition, it is well-known that X-ray radiation can be measured during a sterilization, for example the X-rays which occur when the electrons strike a surface, and, in this way, to correlate the measurement signals with the treatment time and thus also the dose applied. In this case, for example, emitters or containers which are moved past on a sensor installed in a fixed manner can generate a time-modulated signal.

Conventional approaches can provide for a sensor to be arranged in a fixed position with respect to an emitter window when the emitter is mounted in a fixed manner for example. This has the drawback, however, that the measurement can take place only when a container is not present between the emitter and the sensor. The measurement therefore takes place before or after the sterilization. If the sensor is positioned immediately in front of the emitter window, it intercepts part of the radiation which then cannot be used for the sterilization.

In other methods, the emitter is movable, for example, attached to a turntable in a fixed position. The current is measured only when the emitter passes the sensor. The current sensor can be mounted in a fixed manner in this case on the radiation devices, for example the radiation fingers. In this case too, however, the sensor intercepts a considerable part of the electrons and forms shadows on the surface to be sterilized. In addition, there is an additional outlay in positioning the cables for the measurement since the emitter has to be sufficiently small to be capable of being passed through openings in the container.

The monitoring of the emitter parameters such as current and voltage has a drawback in that conventional apparatus cannot monitor the quality of the irradiation. By way of example, the electron beam could not strike the emitter window in a uniform manner, the beam profile may be non-homogeneous, and part of the electrons emitted can be intercepted in the an alternative approach for measuring emitter housing.

An alternative approach for measuring X-ray radiation is described in German patent application DE 2009 034 646 A1 incorporated by reference herein, namely, including a radiation head with a vacuum housing. In this case a monitoring device is provided by which at least one operating parameter of the radiation head is capable of being detected and a failure prediction figure is capable of being derived from this by comparison with at least one reference value. The radiation device itself is checked in the case of this apparatus. In this case, a sensor system can be provided which is fixed relative to the emitter.

An object of the present invention is therefore to monitor the sterilization of containers, in particular, sterilization by means of radiation such as electron radiation without obstructing the actual sterilization procedure.

An apparatus according to embodiments of the inventive concepts includes a conveying device which conveys the containers along a pre-set conveying path. In addition, the apparatus can include a first sterilization device which acts upon at least one area of the containers with radiation in order to sterilize the containers.

In addition, the apparatus can include a checking device constructed and arranged downstream with respect to the first sterilization device along the conveying path of the containers in order to check the sterilization procedure, for example, monitor and/or validate the sterilization procedure.

According to the invention the checking device is used for analyzing at least one gaseous medium occurring in the region of the containers. In this way, the checking device is suitable, in particular, for analyzing a flowable medium and is suitable, in particular, for analyzing a gas, or has a gas analysis device and/or is used for analyzing a liquid medium originating in the interior of the container.

In contrast to conventional devices and methods, embodiments of the present inventive concepts propose that it is not the actual sterilization procedure which is to be measured or checked but the effects afterwards as it were. In more precise terms, the effect of the irradiation can be measured with reference to the gas present in a region or an environment of the container and/or a liquid medium, in particular, removed from the container. The region of the container can be both a region situated outside the container and a region situated inside the container. The liquid medium can be for example a flushing medium with which the container has been flushed after the irradiation thereof.

It is advantageous for the analysis device in accordance with some embodiments to be used for analysis with respect to mass particles released or freed from a wall of the container by the radiation device.

In some embodiments, the checking device is suitable for checking an on-line monitoring of the sterilization procedure, i.e., in particular during the working operation and in a particularly preferred manner even during the sterilization procedure. It is advantageous for the radiation to be ionizing radiation and in a particularly preferred manner electron radiation. Alternatively, or in addition, X-ray radiation or UV radiation could be used for the sterilization of the containers. The radiation can include electron beams (E-beams). In this case the surfaces to be disinfected are subjected to a beam of electrons (in particular accelerated). As a result of the interaction of these electrons with germs or the spores thereof, the latter are deactivated and are stopped in their ability to multiply. The safety of the process of electron sterilization for each individual container is demonstrated by the checking device according to embodiments of the invention. It is advantageous for the checking device to be used for the analysis of at least one gaseous medium occurring in the region of each individual container. It is advantageous for the effect of the irradiation to be measured with reference to the gaseous medium or the air respectively.

In other embodiments, the checking device is suitable and provided for analyzing—for each individual container which has also been sterilized by the radiation—a gas occurring in the region of this container, and/or a liquid removed from the container.

In some embodiments, the container is a plastics material container. The container can be a bottle or a plastics material pre-form (which can be converted into a bottle). Substances can be released from the polyethylene terephthalate (PET) or related matter within the scope of an electron beam treatment. Electron radiation has a certain depth of penetration in surfaces and causes different effects there. Depending upon the material, polymers can be cross-linked or degraded. In each case there is an introduction of energy which has a chemical and/or physical interaction on the surface.

In the case of irradiation with electrons, various substances are produced for example in the PET and are released from the polymer, which can subsequently leave the surface. In this way, in the framework of tests for example, containers have been irradiated and then filled with ultrapure water. In a subsequent analysis bisphenol A, isobutyl phthalate, acetaldehyde and further higher hydrocarbons such as octadecane, tricosane, tetracosane, eicosane, and so on, the concentrations of which correlate to the radiation dose irradiated, have been found in this case in small quantities inter alia in this water. In the case of a further procedure it is possible for the container to be flushed internally after the sterilization procedure and for the flushing medium, for example, liquid, then to be analyzed. In this method the proof is thus made by way of a successful irradiation by a liquid or water analysis (in particular continuous). This analysis is thus preferably also carried out in line or during the working operating of the plant.

The inventive concepts make use of this effect in that it measures the gas or the air, in particular in the region of the container which has been sterilized. In particular the container is a PET container.

As mentioned herein, the existing concentrations of the substances released from the material are very small. Nevertheless it is possible for the containers to be blown out after the irradiation. The substances can, however, be measured or detected by the checking device before the blowing out or with the blowing out.

In preferred embodiments, the sterilization device can act upon an outer wall or inner wall of the container. It is preferable for the sterilization device to have radiation fingers which can be introduced into the interior of the container through the aperture of the container. It is advantageous for the sterilization devices to have electron accelerator devices which accelerate electrons. In addition, the sterilization devices preferably also have exit windows, in particular titanium windows, through which electrons can emerge from the sterilization devices.

In this case it would be possible for the sterilization devices to be moved jointly with the containers, for example in the form of radiation fingers which dip into the container. It is possible for the sterilization devices to be arranged in a stationary manner, for example, in a fixed position relative to a movement of the conveying path P. In addition, a plurality of sterilization devices can also be provided which permit both an external sterilization and an internal sterilization of the containers.

It is advantageous for the apparatus to have a clean room, inside which the containers are sterilized and/or the sterilization is checked. It is advantageous for this clean room to extend along at least one portion of the conveying path of the containers. It is advantageous for the clean room to extend both over the region of the sterilization and over the region of the checking of the sterilization.

In other embodiments, the apparatus has a temperature measuring instrument for measuring an internal temperature inside the sterilized containers and/or a temperature of the immediate surroundings of the containers. The temperature can have in this case an effect upon the evaluation of the analyzed gas.

In other embodiments, the checking device has a take-up element or a probe for taking up, or drawing, at least part of the gaseous and/or liquid medium. In this case use could be made of a so-called "sniffer" as is known from inspection technology. These apparatus draw in a certain quantity of the gaseous medium in order to analyze it. In this case the measurement can take place by way of an intake tube which draws in air, or gas and/or liquid from the environment of the container or from the interior of the container and passes it on to the actual checking device.

The checking device can be trained in a suitable manner, so that the measured concentrations of individual molecules can be associated with the dose applied. In addition, an air flow, which releases the substances and supplies them to the "sniffer" mentioned above, can be directed through the containers with the aid of a blasting device.

In other embodiments, the apparatus has a separating device for separating out containers from the conveying path. Here, a separating device can separate those containers which have been recognized by the checking device as being not sterilized or not sufficiently sterilized. The separating device can be arranged downstream of the checking device along the conveying path.

In other embodiments, the checking device has a mass spectrometer. With the aid of this mass spectrometer individual components of the air taken up or the gas taken up can preferably be analyzed and in this way conclusions can be drawn on the efficiency of the sterilization procedure. In general, the checking device is suitable for recognizing components of the gas to be analyzed and/or for determining them with respect to their quantitative proportion. In addition to or instead of a mass spectrometer, however, other checking devices are possible, such as for example optical checking devices.

Since the quantity of the substances released is directly linked to the dose applied, it is possible in this way to establish in a reliable manner whether the respective container has received an adequate dose. In this way, precisely those substances which are released by the electron irradiation should serve as evidence during the sterilization of the container that they have diffused out and that the process has therefore taken place in an adequate manner.

In other embodiments, the checking device is arranged in a stationary manner. In this way, the checking device can be arranged for example slightly above the containers and, in particular, can test an area around the aperture or a medium occurring about the aperture and/or in the container, for example, a gaseous medium.

It is advantageous for the checking device to have a drawing-in element for drawing in at least one pre-set portion of the gaseous medium. This gaseous medium drawn in through the drawing-in element is analyzed accordingly.

In other embodiments, the checking device has a control device which causes a gaseous medium to be drawn in at least in part and/or a gaseous medium to be discharged at least for a time. In this way, it is possible for the gaseous medium first to be drawn in, to be analyzed and then—advantageously completely again—to be discharged, so that a further analysis (with a following container) can take place, without this being falsified by residues of the gas required for the analysis of the preceding gas.

It is advantageous for the control device to control the drawing in and/or discharge of the gaseous medium in a manner dependent upon the conveying of the containers. In this way, for example, a drawing in can take place when a specific container is present in the region of the checking device and the discharge can take place in particular in an intermediate space between two containers. It is thus advantageous for the conveying device to convey separately the containers to be sterilized.

In other embodiments, at least one area of the checking device is present at least for a time at an area of the apertures of the sterilized containers. In this way, it is possible for the checking device to be arranged for example above the conveyed containers or laterally with respect to the conveyed containers and for the containers to be conveyed in each case past the checking device.

In other embodiments, the apparatus has at least one blasting device for blowing out the containers. In this case it is possible for this blasting device to be arranged downstream of the checking device and for the container to be cleaned by blowing out after the checking procedure. It is possible for the blasting device to be arranged in such a way that the checking takes place simultaneously or after the blowing out. It is possible for example for the gas which is to be analyzed to be forced out of the container by the blowing out of the containers.

An under-pressure generating device and, in particular a pump, can be provided which generates an under-pressure in a region of the checking device. It is preferable for a line device, in particular, a capillary, to be provided by way of which the gas to be tested can be supplied to the checking device. In addition, it is advantageous for a removal device to be provided which withdraws the gas to be analyzed out of an analysis room again. This removal device can be for example a vacuum pump.

In addition, the checking device can have an ionizing device which ionizes at least in part the gas to be analyzed. In some embodiments, the checking device has a quadrupole spectrometer which sorts the gas to be analyzed in accordance with its (parts by) weight in order to identify according to their part molecules determined in this way. It is preferable for a permanent gas flow to take place which is drawn in through the capillary or the line device respectively. This gas flow can be tested, in particular, permanently, for the presence of a specified molecular mass. If it is not possible or desired for the capillary to be introduced into the container for sniffing, a defined gas can also be blown into the container and the air flowing out can be tested outside the container for admixtures of the relevant molecules. In this case, the blasting device can move jointly with the respective containers or it can also be arranged in a stationary manner.

Embodiments of the present inventive concepts further relate to a method of sterilizing containers, in which the containers are conveyed along a pre-set conveying path by means of a conveying device and in which at least one area of the containers is irradiated by means of a sterilization device and in which at least part of the containers are checked by means of a checking device with respect to the irradiation procedure after the irradiation. In this case, the checking device is arranged downstream of the sterilization device along the conveying path.

According to embodiments of the inventive concepts, the checking device analyzes at least part of a flowable medium present in an area of the container, in particular, part of a gaseous medium and/or at least part of a liquid medium originating in the container.

In some embodiments, the checking device can have a mass spectrometer. In this way, the checking device advantageously analyzes the gas occurring and/or the liquid originating in the container with respect to different properties of the molecules thereof, for example, the masses of the molecules which occur.

In other embodiments, methods can be performed where the checking device delivers at least one figure which is characteristic of the analysis of the gas occurring. This can be for example one or more figures which is characteristic of molecules of the analyzed gas which occur. It is advantageous for the checking device to deliver at least one figure which is characteristic of the mass portion of a specified molecule.

In other embodiments, the checking device has at least one comparator device which compares at least one figure determined by the checking device with a stored figure and, in a particularly preferred manner, delivers a result or a statement in a manner dependent upon this comparison.

In other embodiments, the checking is carried out with reference to foreign substances caused by the radiation or with reference to the plastics materials released from the plastics material of the containers by the radiation.

In other embodiments, the checking device analyzes the gaseous medium and/or the liquid medium during a movement of the containers.

It is advantageous for a testing time to be <100 ms, preferably <10 ms and preferably <1 ms and in a particularly preferred manner <0.2 ms. The actual measurement time is also dependent upon the desired measurement results. In a measurement time of between 1 and 10 ms weak concentrations or a multiplicity of substances can be shown simultaneously.

It is advantageous for a measurement to be carried out in-line, i.e. in particular for each individual container in the production. In this way, an in-line process monitoring for the sterilization of the containers is advantageously carried out.

In other embodiments, a method can be performed where the checking device draws the gaseous medium in at least for a time. This medium drawn in in this way is preferably analyzed.

In other embodiments, a method can be performed where a gaseous medium is blown into the containers before and/or during the checking of the gaseous medium by the checking device. This gaseous medium can be for example a filtered gas, clean air, an inert gas, a noble gas or even a mixture of noble gases. In this case, a mixture can have, in a particularly preferred manner, precisely known molecule portions and is used in a particularly preferred manner for forcing the gas formed during the sterilization out of the container.

It is advantageous for a portion of the gas mixture forced out of the container in this way to be tested or analyzed respectively.

FIG. 1 shows an apparatus 1 according to an embodiment related to the sterilization of containers 10. The containers 10 are supplied to the apparatus 1 along a conveying path P, for example, first by way of a supply device such as a supply wheel 24. The containers 10 are then sterilized by a sterilization device 4 during a movement along the conveying path P by a second conveying unit 22. In FIG. 1, a sterilization of the external surfaces of the containers is shown as occurring, but in addition or as an alternative, an internal sterilization of the containers can take place with this portion.

The second conveying unit 22 can include a conveying wheel on which the containers 10 are conveyed. It is possible in this case for two or more sterilization devices 4 to be provided which are arranged on the conveying wheel 22 and thus move jointly with the container 10. The conveying device 2 can include some or all of these elements.

Another conveying unit 26, also referred to as a second conveying unit, which can be a component of the conveying device 2, can remove the containers already sterilized. A checking device 6 can check a sterilization procedure of the containers 10, and can be arranged in the region of the other conveying unit 26. The checking device 6 can analyze a gas or air in the region of the containers 10. This checking device 6 can include a probe 64—in particular designed in the form of a drawing-in device—by means of which the gas can be drawn in the region of the containers. A control device 66 can control the checking device 6. The control device 66 can advantageously control the checking device 6 also in a manner dependent upon the conveying of the containers 10. In this manner, for example, a gas can be drawn in or discharged again in each case in a manner dependent upon a relative position of the containers with respect to the drawing-in device 64.

The checking device 6 can include a comparator device 68 which compares an analysis result of the gas taken up with a pre-set stored figure. The result, which indicates whether a correct sterilization of the containers 10 has taken place, can be delivered to the user in a manner dependent upon this comparison. The checking device 6 can include a memory device in which reference data for the gas to be analyzed is advantageously stored. A processor can be provided for processing the stored data. Different reference data can be stored for example for different containers or container materials.

Figure 2:
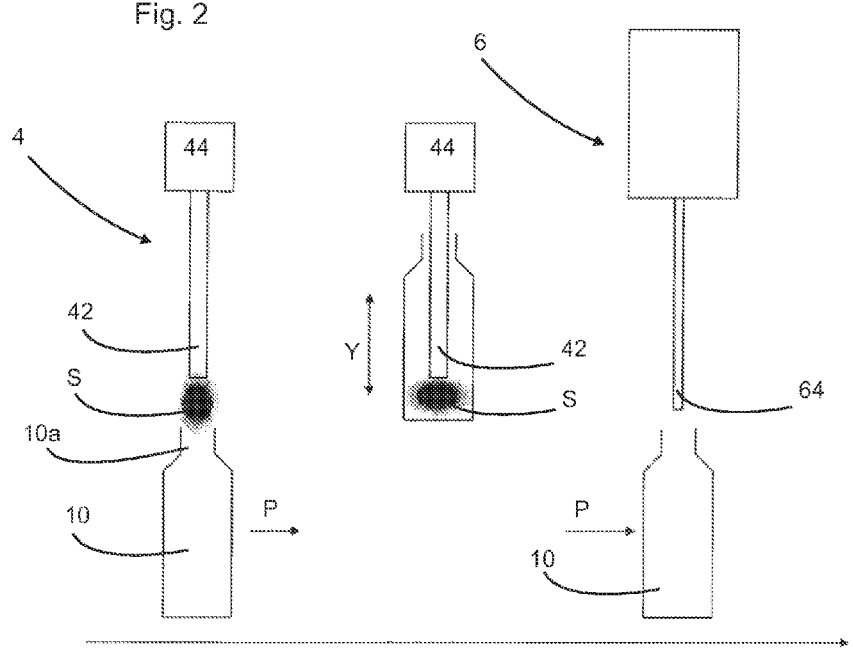
FIG. 2 is a detailed illustration of an apparatus for sterilization containers.

FIG. 2 illustrates an embodiment of an apparatus according to the inventive concepts. In FIG. 2, the sterilization device 4 can include a radiation device that has an electron accelerator 44 as well as a radiation finger 42 which is capable of being introduced into the interior of the containers 10. In doing so, radiation beams S can emerge from the radiation finger 42 and which, as in this case, strike an inner wall of the container 10 in a particularly preferred manner. An aperture 10a of the container 10 is provided through which the radiation finger 42 is introduced into the container 10.

It is thus preferred for the conveying device 2 also to have holding elements (not shown) which hold the containers and which can lift them in the direction Y, so that the radiation finger 42 dips into the interior of the containers 10 in this way.

The checking device 6 can be again arranged downstream with respect to the radiation device 4 in the conveying direction P. In this case the drawing-in element or a probe 64 is arranged above the apertures 10a of the containers 10 and thus takes up a gas which is present for example in the container 10 or emerges from the latter.

In addition, a blasting device can also be provided which blows the gas out of the container 10.

The applicants reserve the right to claim all the features disclosed in the application documents as being essential to the inventive concepts, insofar as they are novel either individually or in combination as compared with the prior art.

What is claimed is:

1. An apparatus that sterilizes a plurality of containers, comprising:
a conveying device that conveys the containers along a pre-determined conveying path;
a first sterilization device that sterilizes at least a portion of the plurality of containers with radiation; and
a checking device constructed and arranged downstream with respect to the first sterilization device along the conveying path for checking a sterilization procedure, wherein the checking device analyzes at least one gaseous medium occurring in a region proximal to the plurality of containers or a liquid medium in an interior region of at least one of the plurality of containers, wherein the gaseous medium comprises substances released from irradiating containers, wherein the checking device analyzes mass particles of the substances released or freed from a wall of a container of the plurality of containers by the first sterilization device, and wherein the checking device includes a gas analyzing device.

2. An apparatus according to claim 1, wherein the checking device includes a take-up element for drawing at least part of the gaseous medium or the liquid medium.

3. An apparatus according to claim 1, wherein the checking device includes a drawing-in element for drawing in at least one pre-set portion of the gaseous or liquid medium.

4. An apparatus according to claim 1, wherein the checking device includes a mass spectrometer.

5. An apparatus according to claim 1, wherein the checking device is constructed and arranged in a stationary position relative to a movement of the conveying path.

6. An apparatus according to claim 1, wherein the checking device includes a control device that causes a gaseous medium to be drawn in at least in part and/or a gaseous medium to be discharged at least for a time.

7. An apparatus according to claim 1, wherein the checking device is at least temporarily present in an area proximal to apertures of the sterilized containers for testing an area around the apertures or a medium thereabout or therein.

8. An apparatus according to claim 1, wherein the apparatus has at least one blasting device for cleaning the containers.

9. An apparatus according to claim 1, wherein the liquid medium is a flushing medium with which the container is flushed after the irradiation thereof.

10. An apparatus according to claim 1, wherein a clean room extends along at least one portion of the conveying path of the containers.

11. An apparatus according to claim 1, wherein a clean room extends over both a region of sterilization and a region of checking of the sterilization.

12. An apparatus according to claim 1, wherein the checking device includes an ionizing device which ionizes at least part of the gas to be analyzed.

13. An apparatus according to claim 1, wherein the checking device includes a quadrupole spectrometer which sorts the gas to be analyzed in accordance with a weight in order to identify according to part molecules determined in this manner.

* * * * *